United States Patent [19]

Crawford

[11] Patent Number: 4,573,977
[45] Date of Patent: Mar. 4, 1986

[54] BLADDER-TYPE SYRINGE

[76] Inventor: A. Gerrit Crawford, 6223 Bakman St., North Hollywood, Calif. 91606

[21] Appl. No.: 583,775

[22] Filed: Feb. 27, 1984

[51] Int. Cl.$^4$ ............................................. A61M 1/00
[52] U.S. Cl. ..................................................... 604/212
[58] Field of Search ............... 604/212, 214, 216, 192, 604/187, 28, 200–204

[56] References Cited

U.S. PATENT DOCUMENTS

| | | | |
|---|---|---|---|
| 401,950 | 4/1889 | Haussmann | 604/214 |
| 2,781,951 | 2/1957 | Hanford | |
| 2,907,326 | 10/1959 | Gerarde | 604/214 |
| 3,867,923 | 2/1975 | West | 604/214 |
| 4,410,323 | 10/1983 | Hodosh et al. | 604/212 |

Primary Examiner—C. Fred Rosenbaum
Assistant Examiner—Christa K. Scott

[57] ABSTRACT

The present invention is a bladder-type syringe which a user employs to collect blood samples or deliver prefilled medications or function as a passive indicator of balloon or cuff inflation on balloon-tipped catheter or endotracheal tubes. The bladder-type syringe includes an elongated bladder and a hypodermic needle. The elongated bladder is formed out of a high gas-diffusion barrier film and has an open end and a closed end. The hypodermic needle, which the user employs to penetrate into a blood vessel, has a sharp distal end and a blunt proximal end. A coupling device fixedly, but detachably, and fluidly couples the elongated bladder at its open end to the hypodermic needle at its blunt proximal end which extends into the coupling device to reduce its dead space. The bladder-type syringe also includes an elongated member having a first end and a second end and also having a flat surface with a keeper slot at its first end. The elongated bladder is fixedly, but detachably, coupled to the keeper slot. The user is able to support the elongated bladder and isolate any air bubbles contained in the elongated bladder. The coupling device is mechanically coupled to the elongated member at its second end so that the elongated bladder is suspended above the flat surface of the elongated member. The elongated bladder has longitudinal convolutions whereby the amount of gas contained within the elongated bladder is minimized when the elongated bladder is empty.

4 Claims, 4 Drawing Figures

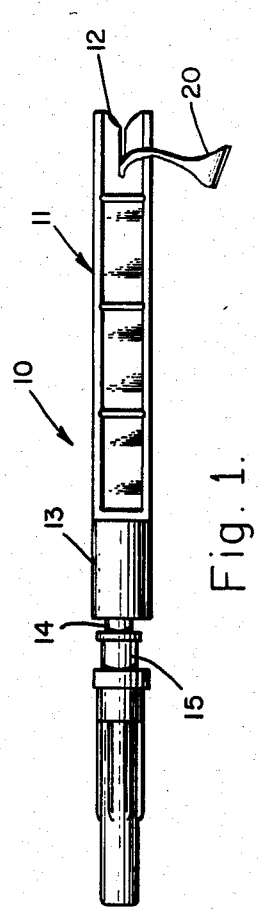
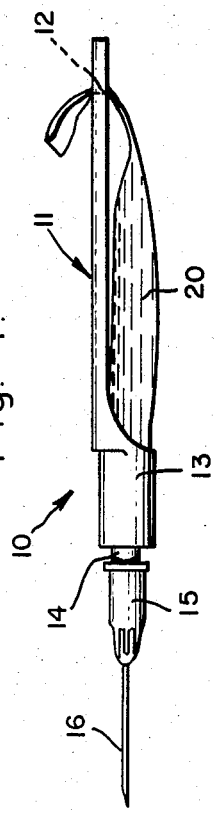
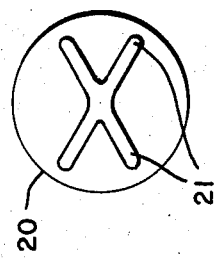
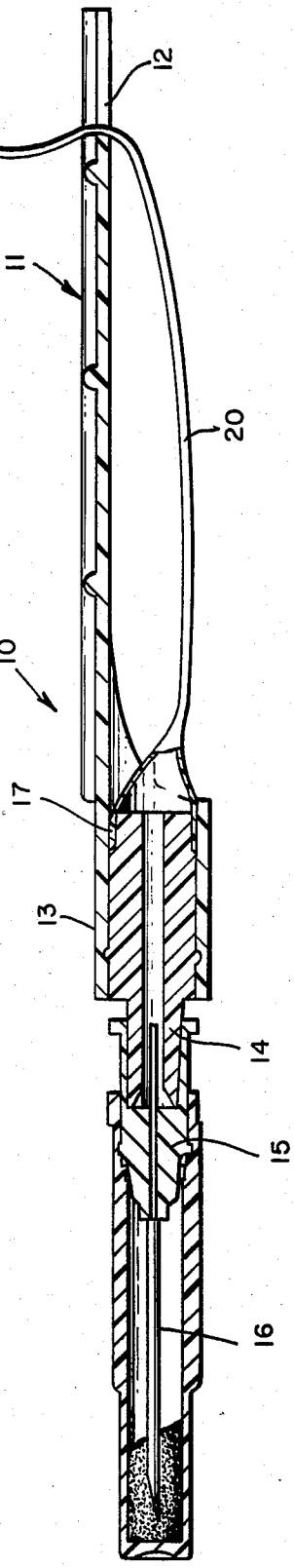
Fig. 1.
Fig. 2.
Fig. 3.
Fig. 4.

BLADDER-TYPE SYRINGE

BACKGROUND OF THE INVENTION

1. Field of the Invention

The present invention relates to devices for collecting fluid samples or injecting medications or assessing the degree of inflation of balloon-tipped catheters or endotracheal tubes and more particularly to a bladder-type syringe in which not only is the amount of air, which will contaminate a portion of the fluid sample, therein minimized, but also the contaminated portion of the fluid sample may be separated from its uncontaminated remaining portion.

2. Description of the Prior Art

Human blood samples have long been collected for various medical tests. In recent years, gas-tension analysis of blood has become one of the most important laboratory tests in the management of patients with respiratory and metabolic disorders by measuring the partial pressures of dissolved oxygen and carbon dioxide in the circulatory system. However, the collection of a satisfactory blood sample from a patient for analysis has posed a number of difficulties. Initially in some patients it may be somewhat difficult to ascertain whether the collection device has received arterial or venous blood without differentiating "fill pressures" during collection. Second, the collection device should minimize contact of the blood sample with air since the air may affect the results of blood analysis. It is also desirable that the sample should not be collected in the presence of a vacuum, since it is believed that the vacuum may modify the gas-tension characteristics of the sample. The collection device should also be in a suitable form to permit closure of the sample to air and provide thermal characterisitics which promote rapid chilling of the sample during the period of time between collection and analysis.

In the past, plastic and glass syringes with a needle have been commonly used to collect the blood samples. U.S. Pat. No. 3,930,429 proposes a plastic syringe for distinguishing arterial pressure. However, plastic syringes have proven deficient for such purposes due to the relatively high resistance between the syringe plunger and barrel thereby making it difficult to clearly distinguish that the blood is arterial. The plunger resistance in plastic syringes prevents movement of the plunger responsive to arterial pressure alone and requires that the plunger be manually withdrawn, thus creating an undesirable vacuum in the syringe chamber during collection and requiring plunger manipulation during sampling. Further, since the plungers of plastic syringes are not sufficiently mobile to move under arterial pressure, they did not provide an indication whether arterial or venous blood is being collected. Although glass syringes may be used to detect arterial pressure, the glass syringes are relatively expensive and if the user does not exercise sufficient care, the glass syringe may be easily broken during the blood collection and transport.

Additional problems with prior blood samplers have included diffusion of oxygen and carbon dioxide though the wall of the sampler and around the plunger or venting system thereby causing erroneous readings of the blood gas analysis; the presence of either liquid heparin or air-filled deadspaces in the sampler introduces an error into the analysis of oxygen and carbon dioxide and poor thermal conductivity which inhibits rapid chilling of the sample for transport.

U.S. Pat. No. 3,943,917, entitled Method for Collecting Blood Samples, issued to Ebbe Johansen on Mar. 16, 1976, teaches a blood collection device which includes syringe housing, a plunger with a piston seal and a wedge member. The plunger is inserted into the syringe housing in order to form a collection chamber. U.S. Pat. No. 3,943,917 also teaches a procedure for collecting a blood sample in which the wedge member is inserted between the syringe housing and the piston seal of the plunger thereby deforming the piston seal in order to form a passageway so that air is allowed to escape from the collection chamber as blood enters the collection chamber.

U.S. Pat. No. 4,340,067, entitled Blood Collection Device, issued to Christen C. Rattenborg on July 20, 1982, teaches a syringe for collecting a blood sample which includes a cylindrical housing having a hollow needle at one end. A plunger slidably mounted within the cylindrical housing defines a chamber within which blood collected by the needle is received. A hydrophillic bypass element is disposed between the rim of the plunger and the inside surface of the housing to form a passageway through which air is exhausted as blood enters the chamber under arterial pressure. The passageway is automatically closed to prevent leakage from the chamber when the chamber becomes filled with blood and the hydrophillic bypass element is wetted.

U.S. Pat. No. 4,206,768, entitled Syringe Device with Means for Selectively Isolating a Blood Sample after Removal of Contaminates, issued to Donald L. Bailey on June 10, 1980, teaches a syringe device for drawing blood samples which includes an interrupter.

U.S. Pat. No. 4,326,541, entitled Syringe Device with Means for Selectively Isolating a Blood Sample after Removal of Contaminates, issued to Donald L. Bailey and Charles Williams on Apr. 27, 1982, teaches an improved syringe device for drawing blood samples.

U.S. Pat. No. 4,354,507, entitled Syringe, issued to Russell G. Raitto on Oct. 25, 1983, teaches a disposable syringe for taking arterial blood samples for blood gas testing.

U.S. Pat. No. 4,411,275, entitled Syringe, issued to Russell G. Raitto on Oct. 25, 1983, teaches a disposable syringe for taking arterial blood samples for blood gas testing.

U.S. Pat. No. 4,354,507, entitled Blood Sampling Unit, issued to Frank W. Anastasio on Nov. 30, 1982, teaches a blood sampling unit for sampling arterial blood for purposes of blood gas analysis.

U.S. Pat. No. 4,409,990, entitled Fluid Sampling Needle Assembly and Method of Use Thereof, issued to Gil N. Mileikowsky on Oct. 18, 1983, teaches a fluid transport assembly for collecting arterial blood samples.

U.S. Pat. No. 4,187,860, entitled Arterial Blood Collection Device, issued to Frank K. Villari on Feb. 12, 1980, teaches a blood collection device which includes a housing having a retention space and a hollow needle connected to a distal portion of the housing. The blood collection device has an expansible collection bag defining a collection chamber communicating with the hollow needle. The collection bag is movably responsive to arterial blood pressure between a first configuration of reduced dimensions with air substantially removed from the collection chamber and a second configuration of extended dimensions with the collection chamber enlarged to receive blood.

U.S. Pat. No. 4,266,559, entitled Blood Sampler, issued to David S. Akhavi on May 12, 1981, teaches a blood sampler which particularly suited for collecting and dispensing an arterial blood sample. A needle is connected to a flexible transparent tube that includes an air exit vent with a nonwet filter so that air, but not blood, can exit the vent under arterial blood pressure. A special needle adapter prevents formation of air bubbles, and a baffle clamp on the reservoir pinches off an air contaminated blood segment and can longitudinally strip a different blood segment which is not air contaminated. The tubular reservoir has an oxygen blocking coating, and its internal surface includes a dry anticoagulant coating.

SUMMARY OF THE INVENTION

In view of the foregoing factors and conditions which are characteristic of the prior art it is the primary object of the present invention to provide a bladder-type syringe for collecting a fluid sample in which the amount of air, which will contaminate a portion of the fluid sample, is therein minimized.

It is another object of the present invention to provide a bladder-type syringe for collecting a fluid sample in which the contaminated portion of the fluid sample may be separated from its uncontaminated remaining portion.

In accordance with the present invention an embodiment of a bladder-type syringe for collecting blood sample samples or delivering prefilled medications or functioning as a passive indicator of balloon or cuff inflation on balloon-tipped catheter or endotracheal tubes is described. The bladder-type syringe includes an elongated bladder and a hypodermic needle. The elongated bladder is formed out of a high gas-diffusion barrier film and has an open end and a closed end. The hypodermic needle, which the user employs to penetrate into a blood vessel, has a sharp distal end and a blunt proximal end. A coupling device fixedly, but detachably, and fluidly couples the elongated bladder at its open end to the hypodermic needle at its blunt proximal end its blunt proximal end which extends into the coupling device to reduce its dead space. The bladder-type syringe also includes an elongated member having a first end and a second end and also having a flat surface with a keeper slot at its first end. The elongated bladder is fixedly, but detachably, coupled to the keeper slot. The user is able to support the elongated bladder and isolate any air bubbles contained in the elongated bladder. The coupling device is mechanically coupled to the elongated member at its second end so that the elongated bladder is suspended above the flat surface of the elongated member. The elongated bladder has longitudinal convulusions whereby the amount of gas contained within the elongated bladder is minimized when the elongated bladder is empty.

The features of the present invention which are believed to be novel are set forth with particularity in the appended claims.

Other claims and many of the attendant advantages will be more readily appreciated as the same become better understood by reference to the following detailed description and considered in connection with the accompanying drawing in which like reference symbols designate like parts throughout the figures.

DESCRIPTION OF THE DRAWING

FIG. 1 is a bottom plan view of a bladder-type syringe which has been constructed in accordance with the principles of the present invention.

FIG. 2 is a side elevational view in cross-section of the bladder-type syringe of FIG. 1 which has been convoluted and evacuated.

FIG. 3 is a end elevational view of the bladder-type syringe of FIG. 1.

FIG. 4 is a side elevational view of the bladder-type syringe of FIG. 1 which has been filled with a fluid sample.

DESCRIPTION OF THE PREFERRED EMBODIMENT

In order to best understand the present invention it is necessary to refer to the following description of its preferred embodiment in conjunction with the accompanying drawing. Referring to FIG. 1 in conjunction with FIG. 2 a bladder-type syringe 10 includes a needle assembly and an elongated member 11 which has a flat surface and which also has a first end and a second end. The elongated member 11 has a keeper slot 12 at its first end and a mounting structure 13 at its second end. The bladder-type syringe 10 also includes a slip-tip 14 which has a longitudinal bore and which is fixedly coupled to the mounting structure 13. The needle assembly includes a coupler 15 and a hypodermic needle 16 which has a sharp distal end and a blunt proximal end. A user employs the hypodermic needle 16 to penetrate into a blood vessel. The coupler 15 has a needle coupling end and a bladder coupling end. The hypodermic needle 16 is insertedly coupled into the needle coupling end of the coupler 15 so the blunt end of the hypodermic needle 16 extends pass the bladder coupling end in order to reduce dead-spaces in the coupler 15. The coupler 15 is fixedly, but detachably coupled to the slip-tip 14 which has bladder coupling end 17.

Referring to FIG. 2 in conjunction with FIG. 3 the bladder-type syringe 10 further includes an elongated bladder 20 which has an open end and a closed end. The elongated bladder 20 is mechanically coupled to the slip-tip 14 at the bladder coupling end 17 thereof and fluidly coupled at its open end to the hypodermic needle 16 at the blunt proximal end thereof through the longitudinal bore of the slip-tip 14.

Referring to FIG. 2 in conjunction with FIG. 4 the elongated bladder 20 may be fixedly, but detachably, coupled to the keeper slot 12 so that the user is able to support the elongated bladder 20 and suspend it above the flat surface of the elongated member 11. By employing the keeper slot 12 the user is also able to isolate any air bubbles contained in the elongated bladder 20.

Referring to FIG. 3 the user may employ the bladder-type syringe 10 to collect blood samples. The elongated bladder 20 has longitudinal convulusions 21 which minimizes the amount of air which is contained within the elongated bladder 20.

Referring again to FIG. 3 the user may also employ the bladder-type syringe 10 so that it functions as a passive indicator of balloon or cuff inflation on balloon-tipped catheters or endotracheal tubes.

Referring to FIG. 4 when the elongated bladder 20 is filled with a blood sample the minimal amount of air which is trapped within the elongated bladder 20 is isolated by the keeper slot 12. The user removes the blood sample by pressing the elongated bladder 20 between his thumb and the flat surface of the elongated member 11.

Still referring to FIG. 4 the user may also employ the bladder-type syringe 10 to deliver prefilled medications. The user injects the medication by pressing the elongated bladder 20 between his thumb and the flat surface of the elongated member 11.

Referring to FIG. 2 in conjunction with FIG. 4 the elongated bladder 20 is formed out of a high gas-diffusion barrier film, such as either vinylidine chloride co-polymers or a metal foil. The barrier film provides profound resistence to diffusion of gas into and out of the elongated bladder 20. The cohesion and stiffness of the barrier film also provides resistance to filling the elongated bladder 20 with a fluid. The barrier film has a high thermal conductivity so that its use in forming the elongated bladder 20 enhances the ability of the user to chill the blood sample contained therein.

Referring again to FIG. 1 in conjunction with FIG. 2 a needle cap 30 for use in combination with the bladder-type syringe 10 has an internal chamber 31. The hypodermic needle 16 is inserted into the internal chamber of the needle cap 30. The needle cap 30 has a non-coring gell 32 disposed in its internal chamber 31. The non-coring gell 32 occludes the lumen of the hypodermic needle 16 from the atmosphere. The needle cap 30 also functions as a wrench for removing the needle assembly.

U.S. Pat. No. 4,187,860 teaches an arterial blood collection device which includes a longitudinally expansible collection bag defining its collection chamber and communicating with the hypodermic needle. As arterial blood fills up the collection bag it unrolls to provide space in the collection chamber for receiving the arterial blood. The collection bag is movably responsive to blood pressure between a first configuration of reduced dimensions with air substantially removed from the collection chamber and a second configuration of extended dimensions with the collection chamber enlarged to receive blood. An externally attached preformed material strip maintains the collection chamber in a collapsed state unless the collection chamber is communicating with arterial pressure. The material strips generate a constant elastic back pressure on the blood sample. The elastic back pressure inadvertently forces the blood sample out of the collection chamber after the arterial blood collection device has been removed from the artery. A user ejects the arterial blood in the collection bag of the arterial blood collection device by rerolling it.

In contrast, the cohesion and stiffness of the barrier film provides resistance in filling the elongated bladder 20 with a fluid. As blood fills the elongated bladder 20 it radially expands the longitudinal convulusions 21 of the elongated bladder 20 so there is no elastically generated back pressure on the blood sample. A user ejects the blood by pressing the elongatded bladder between his thumb and the flat surface of the elongated member 11.

From the foregoing it can be seen that a bladder-type syringe for collecting arterial blood sample has been described. A user may employs the bladder-type syringe to collect samples from an industrial process. It should be noted that the sketches are not drawn to scale and that diistances of and between the figures are not to be considered significant.

Accordingly it is intended that the foregoing disclosure and showing made in the drawing shall be considered only as an illustration of the principles of the present invention.

What is claimed is:

1. A bladder-type syringe which the user employs to collect blood samples, said bladder-type syringe comprising:
   a. an elongated bladder which is formed out of a high gas-diffusion barrier film and which has an open end and a closed end with said elongated bladder having longitudinal convolutions whereby the amount of gas contained within said elongated bladder is minimized so that when said elongated bladder is filled with the blood sample there is a minimal amount of air trapped therewithin;
   b. a hypodermic needle which has a sharp distal end with and a blunt proximal end and which a user employs to penetrate into a blood vessel;
   c. bladder coupling means for fixedly, but detachably, and fluidly coupling said elongated bladder at its said open end to said hypodermic needle at its said blunt proximal end extending into said coupling means in order to reduce dead-spaces in said coupling means; and
   d. an elongated member which has a first end and a second end and which has a flat surface with a keeper slot at its said first end, said elongated bladddder being fixedly, but detachably, coupled to said keeper slot whereby the user is able to support said elongated bladder and isolate any air bubbles contained in said elongated bladder and said bladder coupling means being mechanically coupled to said elongated member at its said second end whereby said elongated bladder is suspended above said flat surface of said elongated member and whereby when said elongated bladder is filled with a blood sample the user removes the blood sample by pressing said elongated bladder between his thumb and said flat surface of said elongated member.

2. A bladder-type syringe according to claim 1 wherein the user employs said bladder-type syringe to deliver prefilled medications wherein when said elongated bladder is prefilled with the medication, the user injects the medication by pressing said elongated bladder between his thumb and said flat surface of said elongated member.

3. A bladder-type syringe according to claim 1 wherein said bladder-type syringe also comprises a needle cap which has an internal chamber into which said hypodermic needle may be inserted and which functions as a wrench for removing said hypodermic needle.

4. A bladder-type syringe according to claim 3 wherein said needle cap has a non-coring gell disposed in its said internal chamber whereby said non-coring gell occludes the lumen of said hypodermic needle from the atmosphere.

* * * * *